United States Patent [19]

Grieshaber

[11] Patent Number: 4,704,760

[45] Date of Patent: Nov. 10, 1987

[54] SURGICAL BLADE CLEANING DEVICE

[76] Inventor: Herman R. Grieshaber, 2044 Balmoral La., Glenview, Ill. 60025

[21] Appl. No.: 864,069

[22] Filed: May 16, 1986

[51] Int. Cl.$^4$ .............................................. B24B 3/54
[52] U.S. Cl. ................................... 15/218.1; 15/210 B
[58] Field of Search ................... 15/210 R, 218, 218.1, 15/210 B

[56] References Cited

U.S. PATENT DOCUMENTS

| 177,394 | 5/1876 | Hall et al. | 15/218.1 |
|---|---|---|---|
| 885,497 | 4/1908 | Maibaum | 15/39 |
| 1,732,467 | 10/1924 | Gregory | 15/423 |
| 1,901,262 | 3/1933 | Robideau | 15/104 R X |
| 2,121,307 | 6/1938 | Swift | 15/39 X |
| 2,202,516 | 5/1940 | Calleo | 15/104.5 X |
| 2,439,171 | 4/1948 | Kreider | 15/210 B |
| 2,659,922 | 11/1953 | Klein | 15/218 X |
| 2,744,276 | 5/1956 | Chambless | 15/104.92 |
| 2,810,923 | 10/1957 | Desso | 15/210 B |
| 3,428,988 | 2/1969 | Blackburn | 15/160 |
| 3,583,018 | 6/1971 | Fink | 15/104.92 |
| 3,761,984 | 10/1973 | Hauschild et al. | 15/39 X |
| 3,982,357 | 9/1976 | Eldridge et al. | 15/218.1 X |
| 4,023,231 | 5/1977 | Haber | 15/210 B |
| 4,087,878 | 5/1978 | Grieshaber et al. | 15/218.1 X |
| 4,245,367 | 1/1981 | Stoute | 15/218.1 X |
| 4,419,781 | 12/1983 | Meegan | 15/210 B |

FOREIGN PATENT DOCUMENTS

| 975037 | 10/1950 | France | 15/39 |
|---|---|---|---|
| 57351 | 8/1946 | Netherlands | 15/104.92 |
| 338327 | 6/1959 | Switzerland | 15/210 B |
| 290641 | 8/1928 | United Kingdom | 15/39 |

Primary Examiner—Chris K. Moore
Attorney, Agent, or Firm—Neuman, Williams, Anderson & Olson

[57] ABSTRACT

A device is provided which is adapted for use in manually cleaning a soiled segment of a surgical blade. The device includes a hollow casing having a base portion and upwardly extending wall portions that form an elongated slot in an exterior surface of the casing. The slot is arranged so that the soiled segment of a surgical blade may be inserted through the slot into the casing and may be moved longitudinally of the slot. A compressible frictional media is disposed within the hollow casing and is adapted to exert compressive frictional force on the inserted surgical blade segment to effect cleaning thereof when the blade is moved longitudinally of the slot.

5 Claims, 4 Drawing Figures

SURGICAL BLADE CLEANING DEVICE

BACKGROUND OF THE INVENTION

When surgical blades such as knifes, scalpels, cautery blades and the like are used in performing surgery, they often become soiled with particles of tissue, blood, or other matter. These materials can become firmly adhered to the blades and severely hinder their further use in surgery. In addition, any blood or tissue dried on to segments of the blades after surgery can be extremely difficult to remove and may prevent the proper sterilization of the blades. These problems have frequently been avoided by immediately wiping the blades with disposable gauze or other cleaning materials during surgery as the need arises. This procedure, however, requires that the surgeon or his assistant interrupt the surgery to clean the blades, using both hands and taking great care to avoid accidental cuts or injuries. Such a cleaning procedure is not only very disruptive to the surgery, but also requires a significant supply of readily accessible gauze sheets and a convenient place to dispose of the soiled gauze.

Attempts to solve this problem have included a device disclosed in U.S. patent No. 4,087,878, which required the surgeon to insert his blade into a casing through a slot to brush the blade against setae members and then scrape the blade against the reinforced edges of the slot as the blade was withdrawn. This device requires many different parts including a base, a hollow casing, setae arranged in a particular pattern, and a means for reinforcing the slot. The surgeon, in addition, must ensure that the '878 device is correctly aligned and that the soiled portion of the blade is carefully inserted through the proper part of the slot so that the blade is both brushed and scraped to obtain a complete cleaning action. Finally, this device, at times, must be used repeatedly to consistently and completely clean the soiled blades of all adhering tissue and blood.

Other cleaning devices are unsuitable for use with surgical blades as they would damage or dull the sharp edges of the blades or would not adequately clean the blades without a substantial disruption of the surgery. In addition, none of these devices are actually addressed to, suggest, or teach a solution to the problem of cleaning surgical blades. These devices also require the assembly of many different elements, including setae and rollers, before they may be put into practice. The other cleaning devices of this general type are disclosed in: Hall, U.S. Pat. No. 177,394 (1876); Maibaum, U.S. patent No. 885,497 (1908); Gregory, U.S. patent No. 1,732,467 (1924); Robideau, U.S. Pat. No. 1,901,262 (1933); Swift, U.S. Pat. No. 2,121,307 (1938); Calleo, U.S. Pat. No. 2,202,516 (1940); Chambless, U.S. Pat. No. 2,744,276 (1956); Blackburn, U.S. Pat. No. 3,428,988 (1969); Fink, U.S. Pat. No. 3,583,018 (1971); Hauschild, U.S. Pat. No. 3,761,984 (1973); Schabmuller, Dutch Pat. No. 57,351 (1946); Royer, French Pat. No. 975,037 (1950), Roze, British Pat. No. 290,641 (1928); and Rosselet, German Pat. No. 27,251 (1884).

SUMMARY OF THE INVENTION

The object of the invention is to provide a simple and inexpensive device that will more efficiently and effectively remove particles of tissue, blood and the like from surgical blades. This is done without the use of numerous parts including setae that must be arranged in a pattern, or special reinforcing elements that must be consciously utilized by the surgeon to obtain the maximum cleaning action. The invention also does not require the careful placement of the surgical blade into a particular portion of the slot formed on the device, and each use cleans the blade more completely than is possible with the prior devices.

It is a further object of the invention to provide a surgical blade cleaning device that is compact and sturdy, and can be easily positioned during surgery without interfering with the activities of the surgeon or assisting personnel.

It is a still further object of the invention to provide a single surgical blade cleaning device that may be used repeatedly during surgery and then may be easily discarded.

It is a still further object of the invention to provide a surgical blade cleaning device that may be used without significantly disrupting the surgical procedure.

It is a still further object of the invention to provide a surgical blade cleaning device that allows the user to clean surgical blades without contacting the soiled portion of the blade with his hands.

It is still a further object of the invention to provide a surgical blade cleaning device that will accommodate a variety of types and sizes of surgical blades.

Further and additional objects will appear from the description, accompanying drawings, and appended claims.

One embodiment of the improved device for cleaning a soiled segment of a surgical blade includes a hollow casing having a base portion and upwardly extending wall portions that form an elongated slot in an exterior surface of the casing. The slot is arranged so that the soiled portion of a surgical blade may be inserted through the slot into the casing and may be moved longitudinally of the slot. A compressible frictional medium is disposed within the hollow casing and is adapted to exert compressive frictional force on the inserted surgical blade segment to effect cleaning thereof when the blade is moved longitudinally of the slot.

DESCRIPTION

For a more complete understanding of the invention, reference should be made to the drawings wherein.

Figure 1:
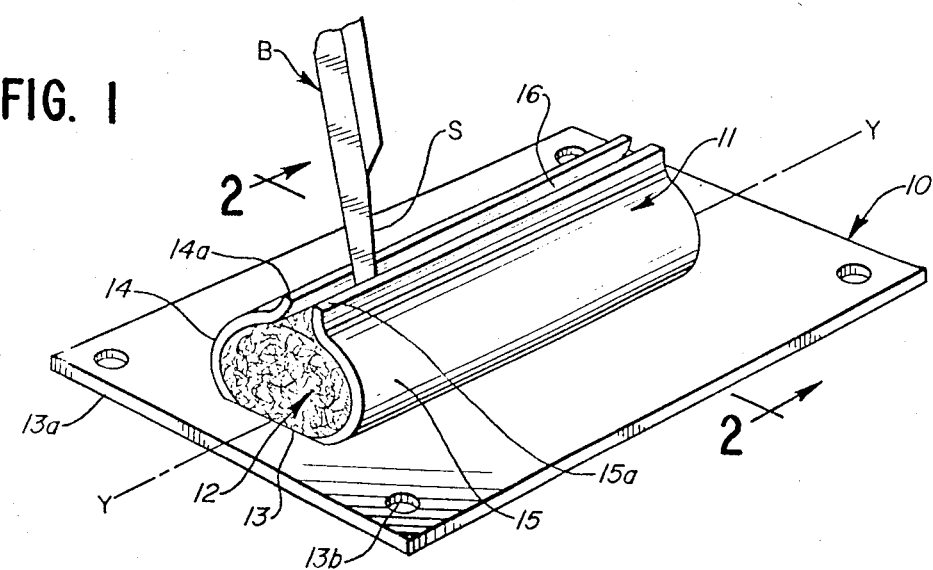
FIG. 1 is a perspective top view of one form of the surgical blade cleaning device showing a soiled end segment of a surgical blade disposed within the slot formed in an exterior surface portion of the device.

Referring now to the drawings and more particularly to FIG. 1, a preferred embodiment of the surgical blade cleaning device 10 is shown for use in cleaning a soiled segment S of a surgical blade B.

During surgery, a surgical blade often becomes soiled with particles of tissue, blood, or other matter. It is necessary during the surgery to repeatedly clean the blade of this material as soon a possible so as to allow further unhindered use of the blade and to allow the blade to be properly sterilized after surgery has been concluded.

The device 10 as shown in FIG. 1 includes an elongated casing 11 and a compressible frictional medium 12 disposed within the casing 11. The casing 11 is preferably extruded from a rigid aluminum material or an inexpensive, semi-rigid, plastic material (e.g. Melamine resin) and includes a base portion 13 and upwardly extending wall portions 14 and 15. The wall portions coact to form an elongated slot 16 on the upper exterior of the casing 11. The slot is disposed in a substantially parallel relation with the longitudinal axis Y—Y of the casing 11. The edges 14a and 15a of the wall portions defining the slot 16 are usually disposed in a relatively spaced, substantially parallel relation. If desired, however, the edges may converge from one end of the slot so as to accommodate different size blades.

The soiled segment S of blade B is normally inserted into one end of slot 16 (the wide end where the edges converge) and is moved longitudinally thereof to the other end; but, if desired, the blade segment S may be inserted into the slot at any point. The longitudinal movement of the soiled segment S in the slot is also not limited and may be in either direction along the axis Y—Y of the casing 11.

The compressible frictional medium 12 is fixedly mounted within casing 11 and extends at least the full length of the slot 16. The medium is preferably formed of either dense wire clusters, abrasive like sponge material, or the like. When the frictional medium is disposed within the casing 11, it is in a compressed state either because the medium is in a compressed state prior to its disposition within the casing 11 and is retained in its compressed state by the casing wall portions 14 and 15, or because the casing walls are resilient and exert an inward compressive force against the medium after its disposition therein. In either case, when the soiled segment S of blade B is inserted into and moved longitudinally of slot 16, the medium 12 will engage surfaces of the soiled segment S and exert compressive frictional force against the segment surfaces and effect cleaning thereof. The cleaning action ensures a consistent and complete stripping or scraping of tissue or blood particles from the soiled segment surfaces without dulling or damaging the sharp edges of the blade B.

The base portion 13 of the casing 11 is preferably of a planar configuration and has a marginal portion 13a thereof extending laterally outward a substantial distance beyond the wall portions 14 and 15. The size of the base portion 13 relative to the entire casing 11 provides stability to the device when it is resting on a table top or other suitable surface. Apertures 13b may be provided at the corners of the marginal portion to allow clamping or pinning of the device to a solid or fabric surface.

Figure 2:
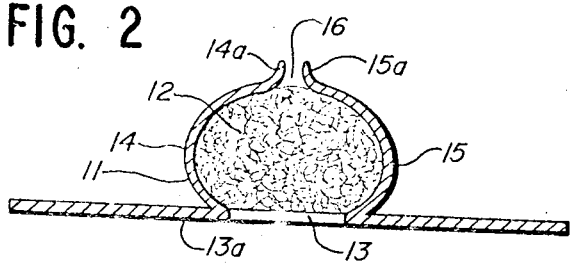
FIG. 2 is an enlarged cross-sectional view of the embodiment taken along the line 2—2 of FIG. 1.

The upwardly extending wall portions 14 and 15 of the casing 11 are preferably formed so that they curve inwardly to give the casing 11 a generally cylindrical cross-section as can be seen in FIG. 2. The edges 14a and 15a of the wall portions adjacent slot 16 are also preferably formed as upwardly extending flanges as shown in FIG. 2 and act to aid the surgeon's placement and longitudinal movement of the soiled segment S of the blade B within the slot 16 to ensure a complete cleaning action.

Figure 3:
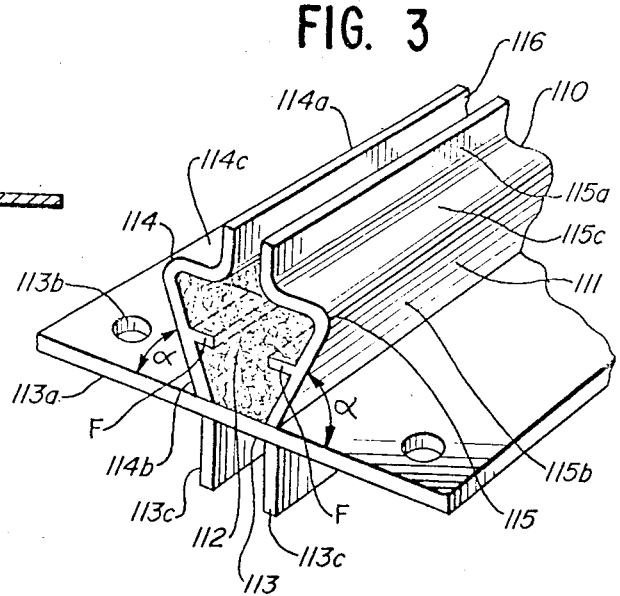
FIG. 3 is a fragmentary, enlarged perspective end view of a second form of the improved cleaning device.

In a modified construction of the device 110 shown in FIG. 3, the upwardly extending wall portions 114 and 115 have lower segments 114b, 115b, and upper segments 114c, 115c. The lower segments extend upwardly and at a like angle α from a base portion 113. The angle α is preferably acute, but need not be so. The upper segments 114c, 115c extend towards one another from the upper edges of segments 114b, 115b and are in substantially coplanar relation so that the casing 111 has a generally trapezoidal cross-section, see FIG. 3.

Disposed on the interior surface of lower segments 114b, 115b are inwardly directed flanges F that act to secure a compressible frictional medium 112 within the casing interior. As with the device 10 shown in FIG. 1, the edge portions 114a and 115a of the wall portions 114 and 115 defining a slot 116 of the device 110, are formed as upwardly extending flanges, and the base portion 113 is of planar configuration with marginal portion 113a thereof extending laterally outwardly a substantial distance beyond the wall portions. The marginal portion 113a may be provided with apertures 113b.

The underside of the base portion 113 may be provided with depending protuberances 113c which facilitate mounting the device on a bedside railing, tray, surgical clamp, or like object. In the illustrated embodiment, the protuberances are in a substantially parallel relation and aligned with slot 116.

Figure 4:
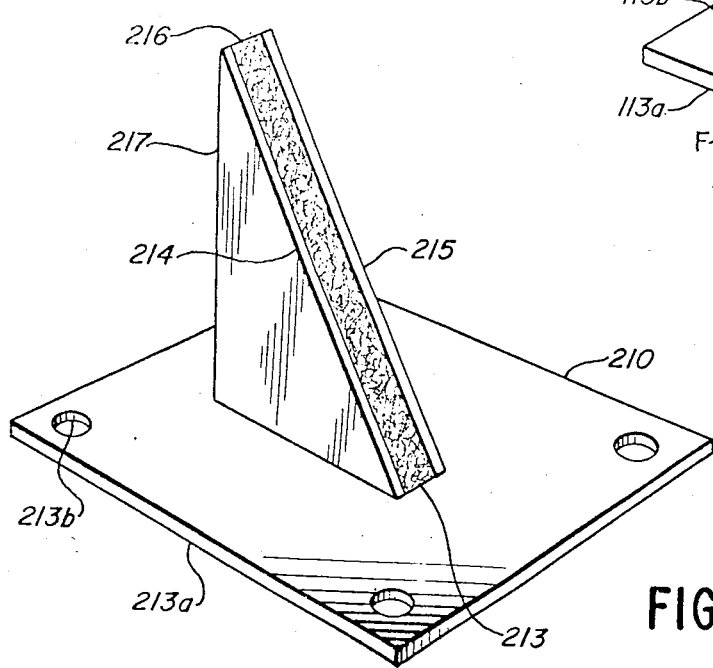
FIG. 4 is an enlarged perspective side view of a third form of the surgical blade cleaning device.

In a modified device 210, shown in FIG. 4, the wall portions 214 and 215 extend upwardly from a base portion 213 and are formed in the shape of right triangles. The longest or hypoteneuse sides of walls 214 and 215 are adjacent the slot 216. The device 210 may also be provided with an upwardly extending end panel 217 opposing slot 216, and delimited by the walls 214 and 215. The base portion 213 may also have a marginal portion 213a extending outwardly a substantial distance beyond the walls 214 and 215 to give the device stability and may have apertures 213b so that the device may be fixed to a table top or other such surface. With device 210, the soiled blade segment S is preferably moved downwardly and outwardly along the slot 216. Upon reaching the bottom of the slot the blade is pulled outwardly from the slot.

Thus, it will be seen that a simple and inexpensive surgical blade cleaning device has been provided that will more efficiently and effectively remove particles of tissue, blood and the like from surgical blades. This is done without the use of numerous parts including specially arranged setae or reinforcing elements that must be consciously utilized by the surgeon. The invention does not require the careful placement of the surgical blade into a particular portion of the slot formed on the device, and the blade may be cleaned in either direction of the slot. The invention is compact and sturdy, and can be conveniently positioned during surgery. It may be used repeatedly without significantly disrupting the surgical procedure and may require the use of only one hand. Nor is the user endangered by possible contact with the blades during cleaning. The device will also accommodate a variety of types and sizes of surgical blades and is readily disposable.

I claim:

1. A device for use in cleaning a surgical blade soiled with adherent liquid an non-liquid matter comprising a hollow casing having an exposed surface provided with an elongated narrow slot sized to accommodate and guide the soiled blade portion when the latter is inserted at an acute angle through the slot and moved longitudinally thereof, and a frictional medium disposed within said casing having only a portion thereof aligned with said slot, being only accessible to the blade portion through said slot, and extending the full length of said slot; said medium resiliently engaging a concealed surface of the casing circumjacent the slot and being adapted to exert a compressive frictional force on the inserted soiled blade portion to effect cleaning thereof when the angularly disposed, soiled blade portion is moved longitudinally of said slot.

2. The device of claim 1 wherein the hollow casing has a generally cylindrical cross sectional configuration, and the exposed surface of said casing is provided with upwardly extending guide flanges defining the elongated narrow slot.

3. The device of claim 1 wherein the hollow casing is comprised of a base portion and wall portions having upper and lower segments; said lower wall segments extending upwardly and at a like acute angle from the base portion and said upper wall segments extending inwardly from the upper edge portions of said lower wall segments; said upper wall segments being in substantially coplanar relation forming the exposed surface of said casing.

4. The device of claim 3 wherein the lower wall segments extend upwardly and at a like obtuse angle from the base portion.

5. The device of claim 1 wherein the hollow casing is comprised of a resilient synthetic material formed so that said hollow casing exerts compressive force on the frictional medium.

* * * * *